(12) United States Patent
Aoyama

(10) Patent No.: US 12,035,045 B2
(45) Date of Patent: Jul. 9, 2024

(54) ENDOSCOPE PROCESSOR, INFORMATION PROCESSING METHOD, AND COMPUTER PROGRAM

(71) Applicant: HOYA CORPORATION, Tokyo (JP)

(72) Inventor: Tomonari Aoyama, Tokyo (JP)

(73) Assignee: HOYA CORPORATION, Tokyo (JP)

(*) Notice: Subject to any disclaimer, the term of this patent is extended or adjusted under 35 U.S.C. 154(b) by 84 days.

(21) Appl. No.: 17/775,363

(22) PCT Filed: Jan. 22, 2021

(86) PCT No.: PCT/JP2021/002180
§ 371 (c)(1),
(2) Date: May 9, 2022

(87) PCT Pub. No.: WO2021/153437
PCT Pub. Date: Aug. 5, 2021

(65) Prior Publication Data
US 2022/0385818 A1    Dec. 1, 2022

(30) Foreign Application Priority Data

Jan. 27, 2020 (JP) .................. 2020-010935

(51) Int. Cl.
*H04N 23/68* (2023.01)
*G06N 3/065* (2023.01)
*G06T 7/73* (2017.01)

(52) U.S. Cl.
CPC ......... *H04N 23/6845* (2023.01); *G06N 3/065* (2023.01); *G06T 7/73* (2017.01)

(58) Field of Classification Search
None
See application file for complete search history.

(56) References Cited

U.S. PATENT DOCUMENTS

| | | | | |
|---|---|---|---|---|
| 2007/0273759 A1* | 11/2007 | Krupnick | ............... | H04N 23/00 348/45 |
| 2007/0276183 A1* | 11/2007 | Melder | .............. | A61B 1/00011 600/112 |
| 2009/0103885 A1* | 4/2009 | Fujino | .................. | G11B 27/322 348/E5.022 |
| 2012/0113282 A1* | 5/2012 | Tanaka | ................. | H04N 9/8205 348/220.1 |

(Continued)

FOREIGN PATENT DOCUMENTS

| | | |
|---|---|---|
| JP | 2018-7928 A | 1/2018 |
| WO | 2014/103879 A1 | 7/2014 |

OTHER PUBLICATIONS

International Search Report (ISR) dated Apr. 20, 2021 filed in PCT/JP2021/002180.

*Primary Examiner* — Mark T Monk
(74) *Attorney, Agent, or Firm* — GREENBLUM & BERNSTEIN, P.L.C.

(57) ABSTRACT

A processor for an endoscope includes: a determination unit that determines whether a start condition for starting acquisition of a moving image, which is limited to a predetermined time length and has a resolution equal to or higher than that of a still image captured by an endoscope, is satisfied; and a moving image acquisition unit that starts the acquisition of the moving image when the determination unit determines that the start condition is satisfied.

14 Claims, 7 Drawing Sheets

(56) References Cited

U.S. PATENT DOCUMENTS

2014/0375768 A1  12/2014  Tsuchiya et al.
2018/0110398 A1   4/2018  Schwartz et al.
2018/0343390 A1*  11/2018  Duran .................... H04N 23/71

* cited by examiner

| IMAGE ID | IMAGE | TIME INFORMATION | SUBJECT ID | START CONDITION |
|---|---|---|---|---|
| 1 | 1101101.jpg | **-··· | 999111 | — |
| 2 | 1101201.mp3 | **-··· | 999111 | 1 |
| 3 | 1101202.mp3 | **-··· | 999111 | 3 |
| 4 | 1101102.jpg | **-··· | 999111 | — |
| 5 | 1101203.mp3 | **-··· | 999111 | 1 |
| ⋮ | ⋮ | ⋮ | ⋮ | ⋮ |

# ENDOSCOPE PROCESSOR, INFORMATION PROCESSING METHOD, AND COMPUTER PROGRAM

TECHNICAL FIELD

The present technology relates to a processor for an endoscope, an information processing method, and a computer program.

BACKGROUND ART

An electronic endoscope device that includes an electronic endoscope in which an objective optical system and an image sensor are built in a distal end portion of an insertion tube of the endoscope, and a processor for an electronic endoscope that processes a video signal output from the electronic endoscope and generates a video signal displayable on a monitor has been widely used for diagnosis and the like of a person to be examined. In the processor for an electronic endoscope, for example, image processing such as distortion correction or flaw correction, and various types of signal processing, such as gamma correction, white balance adjustment, or enhancement processing, are performed on captured images to provide a high-quality image suitable for doctor's diagnosis. The doctor makes a diagnosis based on these images.

In the electronic endoscope device, many processes, such as control of the objective optical system and the image sensor and acceptance of various operation requests, are executed, and it is required to execute these processes without any delay. Patent Literature 1 discloses an electronic endoscope system and the like capable of preventing an increase in load, an operation delay, and a data loss of an operating system of a processor without using an expensive CPU.

CITATION LIST

Patent Literature

Patent Literature 1: JP 2018-7928 A

SUMMARY OF INVENTION

Technical Problem

Endoscopic examinations include a case where the diagnosis is made by the doctor during an operation of an endoscope and a case where the diagnosis is made at a later date based on a recorded image. In the case where the diagnosis is made at a later date, the diagnosis is mainly made based on a stored still image as a single picture, and thus, the doctor who makes the diagnosis is required to have high skill and experience. However, recording a moving image from the start to the end of the examination with the image quality equivalent to that of the still image at the time of the operation has a problem that the capacity increases.

An object of the present disclosure is to provide a processor for an endoscope, an information processing method, and a computer program for acquiring a moving image captured by an endoscope and limited to a predetermined time length.

Solution to Problem

A processor for an endoscope according to an aspect of the present disclosure includes: a determination unit that determines whether a start condition for starting acquisition of a moving image, which is limited to a predetermined time length and has a resolution equal to or higher than that of a still image captured by an endoscope, is satisfied; and a moving image acquisition unit that starts the acquisition of the moving image when the determination unit determines that the start condition is satisfied.

Advantageous Effects of Invention

According to the present disclosure, it is possible to acquire the moving image captured by the endoscope and limited to the predetermined time length.

DESCRIPTION OF EMBODIMENTS

The present invention will be specifically described with reference to the drawings illustrating embodiments of the invention.

First Embodiment

Figure 1:
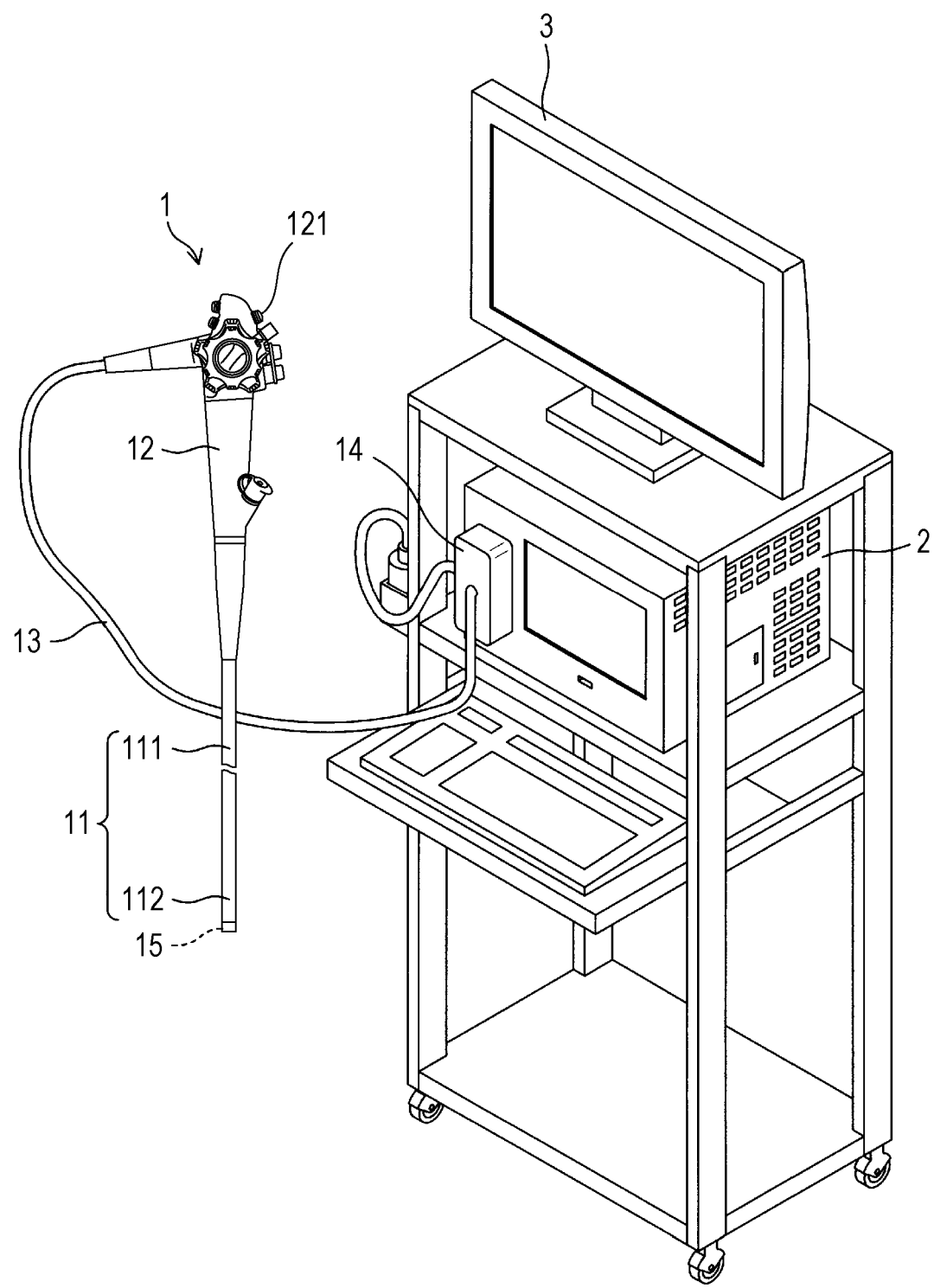
FIG. 1 is a schematic view illustrating an overall configuration of an endoscope system according to a first embodiment.

FIG. 1 is a schematic view illustrating an overall configuration of an endoscope system according to a first embodiment. The endoscope system according to the first embodiment includes an endoscope 1, a processor 2 for an endoscope, and a display device 3. The endoscope 1 is inserted into the inside of a subject and outputs image data of an image, obtained by capturing the inside of the subject, to the processor 2 for an endoscope. The processor 2 for an endoscope performs image processing on the image data input from the endoscope 1, and outputs the image data subjected to the image processing to the display device 3. The display device 3 displays the image of the image data input from the processor 2 for an endoscope. Each of the devices transmits and accepts electric signals, video signals, and the like via a connector.

The endoscope 1 is, for example, an endoscope for an upper digestive tract or a large intestine endoscope. The endoscope 1 includes an insertion portion 11 to be inserted into a hollow organ of a person to be examined, who is the subject, and a scope connector 14 connected to the insertion portion 11 through an operation unit 12 and a universal cord 13, and is used by being connected to the processor 2 for an endoscope by the scope connector 14. An imaging device 15 is built in a distal end part of the insertion portion 11.

The insertion portion 11 includes a flexible tube 111 connected to the operation unit 12 and formed to be relatively long, and a bending section 112 that is bendable, connected coaxially with the flexible tube 111, and formed to be relatively short. A bending mechanism in the bending section 112 is a known mechanism incorporated in a typical endoscope, and is configured such that the bending section 112 is bent by pulling of an operation wire in conjunction with the operation of the operation unit 12. An imaging region of the imaging device 15 moves together with a change in the direction of the distal end part according to the bending operation by the above operation.

The imaging device 15 includes an image sensor such as a charge coupled device (CCD) image sensor or a complementary metal oxide semiconductor (CMOS) image sensor, and an objective optical system for image formation. A driver circuit for driving the imaging device 15 is arranged at a connection part (inside the scope connector 14) with the processor 2 for an endoscope or the like, and includes a central processing unit (CPU), a timing generator (TG), an analog signal processing circuit (AEF), and the like. The driver circuit takes signals of respective colors of RGB output from a solid-state image sensor according to a clock signal output from the TG, and outputs image data of a digital format, obtained by performing necessary processing such as noise removal, amplification, or AD conversion, to the processor 2 for an endoscope.

The operation unit 12 is provided to be gripped by an operator to perform various operations, and is provided with a control button 121 for recording images including a still image and a high-quality moving image. At a timing when the control button 121 is pressed, the endoscope 1 captures a still image and a high-quality moving image of a predetermined time length. The operation unit 12 may be provided with other operation buttons for accepting various operations of the operator in addition to the control button 121. The operation unit 12 outputs an operation signal indicating an operation performed by the operation unit 12 to the processor 2 for an endoscope.

In another embodiment, the operation unit 12 may be configured to independently accept a still image capturing operation and a high-quality moving image capturing operation. For example, the control button 121 is configured to be capable of detecting a two-stage pressing operation of the still image capturing operation and the high-quality moving image capturing operation. The control button 121 accepts the still image capturing operation by the pressing operation in one stage, and further accepts the high-quality moving image capturing operation by being pressed down in another stage. Note that it may be configured such that a plurality of the control buttons 121 are provided to accept the still image capturing operation and the high-quality moving image capturing operation by the different control buttons 121.

The processor 2 for an endoscope is an information processing device for processing image data captured by the imaging device 15 of the endoscope 1 and transmitted through the universal cord 13. The image data processed by the processor 2 for an endoscope is output to the display device 3.

The display device 3 is a liquid crystal display device or an organic electro luminescence (EL) display device, and displays the image data or the like output from the processor 2 for an endoscope.

Figures 2, 3:
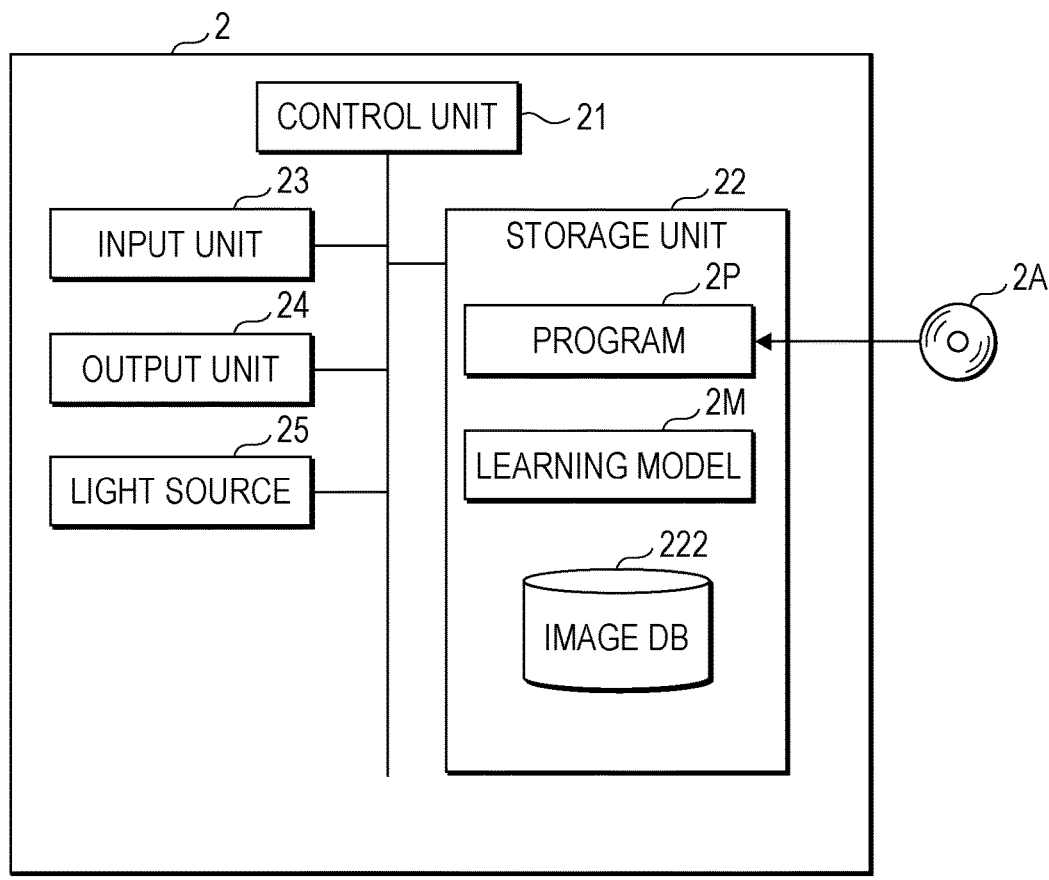
FIG. 2 is a block diagram illustrating a configuration example of a processor for an endoscope.
FIG. 3 is a diagram illustrating a content example of information stored in an image DB.

FIG. 2 is a block diagram illustrating a configuration example of the processor 2 for an endoscope. The processor 2 for an endoscope includes a control unit 21, a storage unit 22, an input unit 23, an output unit 24, a light source 25, and the like.

The control unit 21 includes a central processing unit (CPU), a read only memory (ROM), a random access memory (RAM), and the like. The CPU provided in the control unit 21 functions as the processor 2 for an endoscope in the present embodiment by developing and executing a program 2P stored in the ROM or the storage unit 22 on the RAM.

Note that the control unit 21 is not limited to the above configuration. The control unit 21 may be one or a plurality of arithmetic circuits or control circuits including a graphics processing unit (GPU), a field programmable gate array (FPGA), a digital signal processor (DSP), a quantum processor, a volatile or nonvolatile memory, or the like. In addition, the control unit 21 may have functions such as a clock that outputs date and time information, a timer that measures an elapsed time from when a measurement start instruction is given to when a measurement end instruction is given, or a counter that counts the number.

The storage unit 22 includes, for example, a non-volatile memory such as an erasable programmable read only memory (EPROM) or a recording device including a hard disk. The storage unit 22 stores the program 2P and also stores other programs and data to be referred to by the control unit 21. The storage unit 22 may be configured by a plurality of storage devices, or may be an external storage device connected to the processor 2 for an endoscope. In another embodiment, the storage unit 22 is a portable recording medium such as a USB memory or an SD card, and may be detachable from the processor 2 for an endoscope.

The program 2P may be provided to the processor 2 for an endoscope using a recording medium 2A in which the program 2P is readably recorded. The recording medium 2A is, for example, a portable memory such as a CD-ROM, a USB memory, an SD card, a micro SD card, or a Compact-Flash (registered trademark). In this case, the control unit 21 may read the program 2P from the recording medium 2A through a reading unit (not illustrated) and install the read program 2P in the storage unit 22. Further, in a case where the processor 2 for an endoscope includes a communication unit that communicates with an external device, the program 2P may be provided to the processor 2 for an endoscope by communication through the communication unit. In this case, the control unit 21 may acquire the program 2P through the communication unit and install the acquired program 2P in the storage unit 22.

The storage unit 22 further stores a learning model 2M and an image database (DB) 222. The image DB 222 is a database that registers image information regarding an image captured by the endoscope. The learning model 2M is an identifier that identifies a lesion in the image captured by the endoscope, and is a learning model generated by machine learning. The learning model 2M is defined by definition information. The definition information of the learning model 2M includes, for example, structure information and layer information of the learning model 2M, node information of each layer, and learned parameters. The storage unit 22 further stores the definition information related to the learning model 2M.

The input unit 23 includes a connection interface that connects input devices such as a touch panel, a keyboard, or various switches. The input unit 23 inputs an input signal, generated in response to an external operation on these input devices, to the control unit 21.

The output unit 24 includes a connection interface for connecting the display device 3. An output interface of the output unit 24 may be an output interface that outputs a video signal of an analog format, or may be an output interface that outputs a video signal of a digital format such as a digital visual interface (DVI) or a High-Definition Multimedia Interface (HDMI) (registered trademark). Under the control of the control unit 21, the output unit 24 outputs an image signal for display to the display device 3 to display the image.

The light source 25 includes a light source that emits illumination light used for illuminating an observation target. The light source 25 is, for example, a semiconductor light source such as a multi-color light emitting diode (LED) having a different wavelength range, a combination of a laser diode and a phosphor, or a xenon lamp. In the light source 25, turning-on, turning-off, and a change of luminance are controlled by the control unit 21. Note that the processor 2 for an endoscope is an integrated type of light source in the present embodiment, but the present invention is not limited thereto. For example, the processor 2 for an endoscope may be of a light source separation type that is separated from a light source device.

Furthermore, the processor 2 for an endoscope may include a communication unit. The processor 2 for an endoscope may transmit image data and the like to an external device and accumulate these pieces of information in the external device.

In the present embodiment, the processor 2 for an endoscope will be described as one information processing device, but processing may be performed by a plurality of processors in a distributed manner, or the processor 2 for an endoscope may be configured by a virtual machine.

FIG. 3 is a diagram illustrating a content example of information stored in the image DB 222. The control unit 21 generates a still image and a moving image based on captured image data acquired from the endoscope 1 and stores the still image and moving image in the image DB 222. The image DB 222 stores an image, time information, a subject ID, a start condition, and the like in association with an image ID for identifying an image file.

The image may include an image acquired in an examination by the endoscope 1. In the present embodiment, the image includes a still image and a moving image, and the moving image includes a low-quality moving image and a high-quality moving image. That is, the moving image includes moving images captured by the same imaging device and having different image qualities for the same capturing target at the same time point. The still image is an image acquired and recorded according to an instruction of the operator. The low-quality moving image is an image captured from the start to the end of the examination by the endoscope 1 and recorded with a low resolution. The high-quality moving image is an image acquired according to a predetermined start condition and recorded with a high resolution. Note that the image generated based on the captured image data acquired from the endoscope 1 includes an endoscopic image acquired from the start to the end of the examination by the endoscope 1 and displayed on the display device 3, in addition to the above. The time information includes information indicating a recording time of each image, and stores, for example, a time stamp. The subject ID includes information for identifying a subject that is a capturing target of each piece of captured image data, and stores, for example, a subject ID (patient ID). The start condition includes information indicating a start condition for starting capturing of a high-quality moving image, for example, acceptance of a start operation, detection of a lesion, and a movement amount being equal to or less than a predetermined value. In the example of FIG. 3, the start condition is normalized and registered using one to three type codes. Details of the start condition will be described later. Note that FIG. 3 is an example, and the content stored in the image DB 222 is not limited thereto.

In a typical endoscopic examination, due to a problem of a storage capacity of the processor 2 for an endoscope, a high-resolution still image captured at a predetermined examination location and a low-resolution moving image captured at all times during an operation are generally stored. When a doctor makes a diagnosis at a later date, the doctor makes the diagnosis based on the stored still image. The diagnosis based on the still image as the single picture requires a skilled technique. Therefore, a high-resolution moving image limited to a predetermined time length is further stored in the present endoscope system, so that it is possible to provide a large amount of information by the still image and the moving image recorded with a high image quality even in a case where a diagnosis is made based on stored data.

Figure 4:
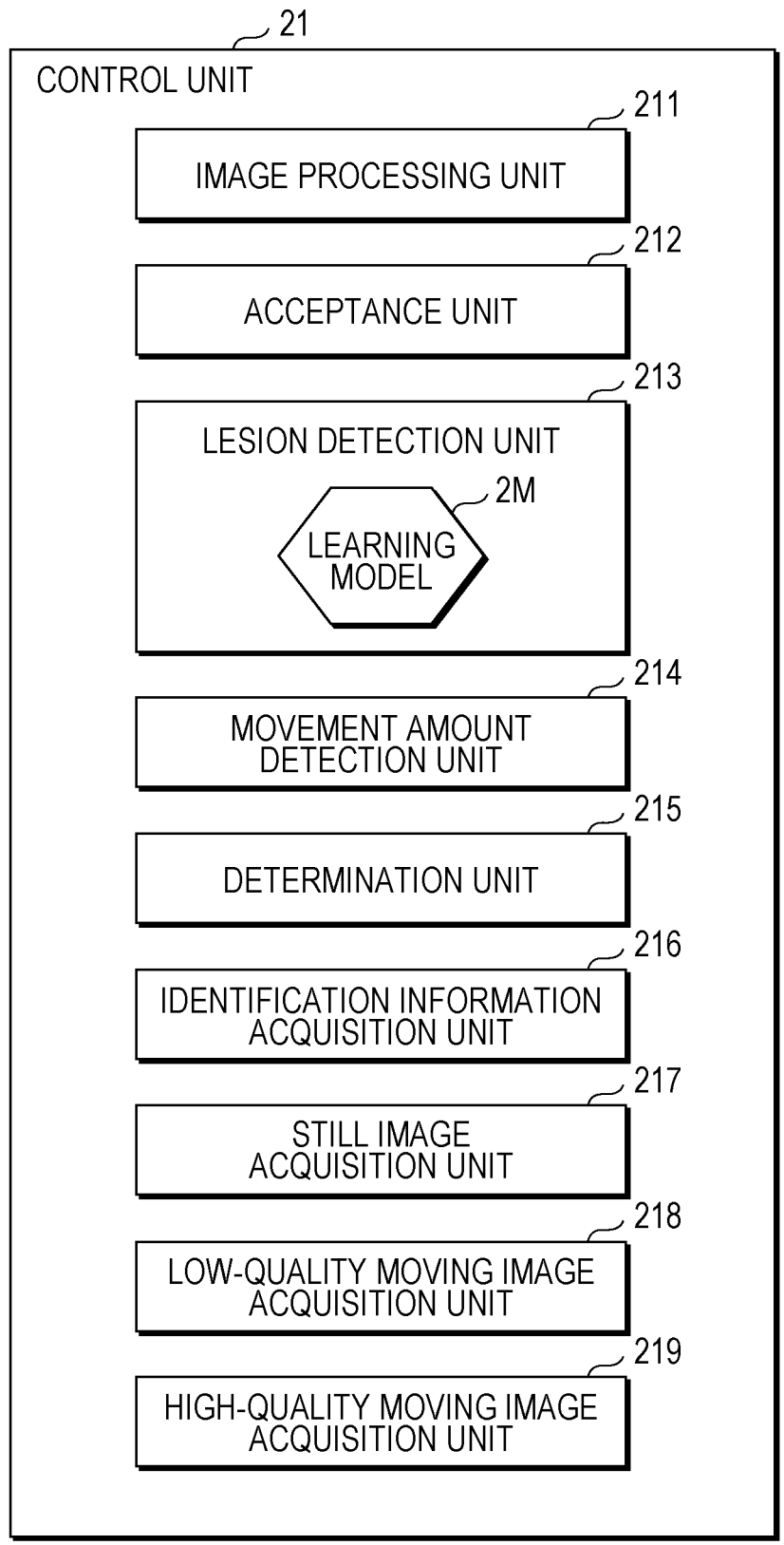
FIG. 4 is a functional block diagram of the processor for an endoscope.

FIG. 4 is a functional block diagram of the processor 2 for an endoscope. The control unit 21 of the processor 2 for an endoscope is configured to function as the image processing unit 211, the acceptance unit 212, the lesion detection unit 213, the movement amount detection unit 214, the determination unit 215, the identification information acquisition unit 216, the still image acquisition unit 217, the low-quality moving image acquisition unit 218, and the high-quality moving image acquisition unit 219 by executing the program 2P stored in the storage unit 22.

Image information for one frame, subjected to various types of processing such as noise removal, is input from the driver circuit of the endoscope 1 to the image processing unit 211 as the captured image data. When the endoscopic examination is started, the image processing unit 211 outputs the captured image data to the still image acquisition unit 217, the low-quality moving image acquisition unit 218, the lesion detection unit 213, and the movement amount detection unit 214 according to control signals output at predetermined intervals from the start to the end. In addition, the image processing unit 211 outputs the captured image data to the still image acquisition unit 217 and the high-quality moving image acquisition unit 219 at a timing an instruction on which is given from the determination unit 215.

The acceptance unit 212 accepts a start operation for instructing the operator of the endoscope 1 to start acquisition of a high-quality moving image. The start operation for given an instruction on the start of acquisition of a high-quality moving image is, for example, a pressing operation of the control button 121. In the present embodiment, the processor 2 for an endoscope acquires a high-quality moving image simultaneously with a still image according to the pressing operation of the control button 121. When the control button 121 of the endoscope 1 is pressed, an operation signal indicating the pressing is input to the acceptance unit 212. The acceptance unit 212 outputs information indicating the acceptance of the start operation to the determination unit 215.

Note that the processor 2 for an endoscope may include a sound input unit such as a microphone (not illustrated), and the acceptance unit 212 may accept the start operation by sound through the sound input unit. The acceptance unit 212 may accept the start operation according to an operation of, for example, a touch panel, a keyboard, or the like input through the input unit 23.

The lesion detection unit 213 outputs a lesion in the captured image data based on the captured image data output from the image processing unit 211. The lesion detection unit 213 includes a function as the learning model 2M learned to output a lesion in designated image data when the image data is input. The learning model 2M will be described later. The lesion detection unit 213 outputs information indicating a lesion detection result to the determination unit 215. Note that the lesion detection unit 213 may detect a lesion using image data obtained by performing various types of image processing on the captured image data. The lesion detection unit 213 may acquire still image data output from the still image acquisition unit 217 to be described later.

The movement amount detection unit 214 detects a movement amount of the endoscope 1 based on the captured image data output from the image processing unit 211. Specifically, the movement amount detection unit 214 detects the movement amount of the distal end part of the insertion portion 11 in the endoscope 1 based on a movement amount of an imaging region included in the captured image data. The movement amount detection unit 214 acquires a frame of the captured image data at a detection time point and a frame immediately before the detection time point, and calculates the movement amount in the same region included in the acquired two frames, thereby detecting the movement amount of the endoscope 1. The movement amount detection unit 214 outputs information indicating a movement amount detection result to the determination unit 215. Note that the movement amount detection unit 214 may detect the movement amount using image data obtained by performing various types of image processing on the captured image data. The movement amount detection unit 214 may acquire the still image data output from still image acquisition unit 217 to be described later.

Note that a method for detecting the movement amount is not limited to the above example. The movement amount detection unit 214 may detect the movement amount of the endoscope 1 based on a captured image using other machine learning methods. For example, the movement amount detection unit 214 may detect the movement amount of the endoscope 1 based on a detection value acquired using a detection sensor, such as an acceleration sensor or a magnetic sensor, provided in the endoscope 1. In addition, the movement amount detection unit 214 may detect a change in an operation amount instead of the movement amount of the endoscope 1. For example, the movement amount detection unit 214 may acquire operation data regarding the operation of the endoscope 1, such as an operation signal of an operation button provided in the operation unit 12, and detect a history of the operation amount of the endoscope 1 based on a log of the acquired operation data.

The determination unit 215 determines whether it is a timing to record a still image and a high-quality moving image, and outputs a determination result to the image processing unit 211. A timing of storing the still image data is a timing immediately after the operator of the endoscope 1 presses the control button 121. When the control button 121 of the endoscope 1 is pressed, the operation signal indicating the pressing is input to the determination unit 215. When the operation signal indicating that the control button 121 has been pressed is input, the determination unit 215 gives a control signal for outputting the captured image data to the still image acquisition unit 217 to the image processing unit 211. Note that the determination unit 215 may acquire information indicating the acceptance of the operation signal (start operation) through the acceptance unit 212.

The timing of storing the high-quality moving image data is a timing immediately after a predetermined start condition is satisfied. The start condition is a condition for starting capturing of a high-quality moving image, and includes a case where a diagnosis is highly likely to be made based on an image captured at a timing when the condition is satisfied. When determining that the start condition is satisfied, the determination unit 215 gives a control signal for starting output of the captured image data to the high-quality moving image acquisition unit 219 to the image processing unit 211.

A first example of the start condition is acceptance of a start operation such as a button operation for giving an instruction on the start of capturing a moving image performed by the operator. The determination unit 215 determines whether the start operation has been accepted based on the information indicating the acceptance of the start operation output from the acceptance unit 212. When acquiring the information indicating the acceptance of the start operation, the determination unit 215 determines that the start condition is satisfied and gives an instruction to start acquisition of high-quality moving image data.

A second example of the start condition is detection of a lesion in an endoscopic image. The determination unit 215 determines whether the lesion has been detected based on information indicating the lesion detection result output from the lesion detection unit 213. When acquiring the lesion detection result indicating that the lesion has been detected, the determination unit 215 determines that the start condition is satisfied and gives an instruction to start acquisition of high-quality moving image data.

A third example of the start condition is detection that the movement amount of the endoscope 1 is equal to or less than a predetermined value. The determination unit 215 determines whether the movement amount of the endoscope 1 is equal to or less than the predetermined value based on information indicating the movement amount detection result output from the movement amount detection unit 214. That is, the determination unit 215 determines whether insertion, a rotation operation, or the like of the endoscope 1 is stopped as the operator continues observation at the same location. In a case where the endoscope 1 remains at the same location, there is a high possibility that a capturing target at the location includes a lesion or the like. When determining that the movement amount of the endoscope 1 is equal to or less than the predetermined value, the determination unit 215 determines that the start condition is satisfied and gives an instruction to start acquisition of high-quality moving image data.

As described above, the start condition includes a plurality of conditions. When determining that any start condition is satisfied, the determination unit 215 gives a control signal for starting output of the captured image data to the image processing unit 211.

The identification information acquisition unit 216 acquires subject identification information, for example, a subject ID or the like. The identification information acquisition unit 216 acquires the subject identification information through the input unit 23 by accepting an input operation of, for example, a keyboard, a touch panel, or the like. The identification information acquisition unit 216 outputs the acquired subject identification information to the still image acquisition unit 217, the low-quality moving image acquisition unit 218, and the high-quality moving image acquisition unit 219.

The still image acquisition unit 217 acquires the captured image data output from the image processing unit 211 at predetermined intervals from the start to the end of the examination. The still image acquisition unit 217 performs various types of image processing such as gamma correction, white balance correction, and shading correction on the acquired captured image data to generate endoscopic images in a state that can be easily viewed by the operator. The still image acquisition unit 217 sequentially outputs the generated endoscopic images to the display device 3 by the output unit 24. A video of the subject is displayed in real time on a display screen of the display device 3, and the operator performs observation based on the endoscopic images.

Further, the still image acquisition unit 217 acquires the captured image data output from image processing unit 211 at a timing according to an instruction from the determination unit 215. The still image acquisition unit 217 acquires the subject identification information output from the identification information acquisition unit 216. The still image acquisition unit 217 generates a still image, obtained by applying predetermined image processing on the acquired captured image data, and acquires the still image as still image data. Note that the still image data may be endoscopic image data acquired at the same time. The still image data is image data having a high resolution such as 1980×1080 (full HD). The still image acquisition unit 217 stores the acquired still image data in the storage unit 22 as a still image file in a predetermined file format, for example, JPEG, TIFF, or the like. In this case, the still image acquisition unit 217 stores the subject identification information in the storage unit 22 in association with the still image data.

The low-quality moving image acquisition unit (a second moving image acquisition unit) 218 acquires the captured image data output from the image processing unit 211 at predetermined intervals from the start to the end of the examination. The low-quality moving image acquisition unit 218 acquires the subject identification information output from the identification information acquisition unit 216. The low-quality moving image acquisition unit 218 performs predetermined image processing including a change in resolution on the acquired captured image data, and generates a low-quality moving image compressed by a predetermined moving image compression method to acquire low-quality moving image data. The low-quality moving image data has a lower resolution than the still image data and the high-quality moving image data. The low-quality moving image acquisition unit 218 stores the acquired low-quality moving image data in the image DB 222 as a low-quality moving image file in a predetermined file format, for example, MP4, MXF, or the like. In this case, the low-quality moving image acquisition unit 218 stores the low-quality moving image data in association with the subject identification information in the storage unit 22.

The high-quality moving image acquisition unit (a moving image acquisition unit) 219 acquires the captured image data output from image processing unit 211 at a timing according to an instruction from the determination unit 215. The high-quality moving image acquisition unit 219 acquires the subject identification information output from the identification information acquisition unit 216. The high-quality moving image acquisition unit 219 acquires captured image data for a predetermined time from an acquisition start timing. The time for which the high-quality moving image acquisition unit 219 acquires the captured image data is, for example, 1 second to 7 seconds, and preferably 5 seconds to 7 seconds. In a case where the acquisition time of the high-quality moving image is 1 second to 7 seconds, image data can be stored with a storage capacity of several tens of megabytes to several hundreds of megabytes even if a frame rate is 30 fsp. Therefore, it is possible to improve the usefulness of information to be provided to the operator while suppressing excessive pressure on the storage capacity. The processor 2 for an endoscope acquires the acquisition time of high-quality moving image data by accepting an input of setting a capturing time of the high-quality moving image in advance by the operator using, for example, a setting screen displayed on a touch panel. Note that the time length for acquiring the high-quality moving image may be determined based on a lower limit value or an upper limit value of the capacity of the high-quality moving image data. That is, the high-quality moving image acquisition unit 219 may start to acquire the high-quality moving image data corresponding to a specific capacity. For example, the processor 2 for an endoscope may derive a resolution and a time length of a high-quality moving image according to a preset acquisition capacity, and acquire moving image data for the derived time length. Note that the processor 2 for an endoscope may acquire image data at a frame rate lower than that of the low-quality moving image data, for example, at the time of acquiring the high-quality moving image data corresponding to a predetermined capacity. As the frame rate is lowered, it is possible to increase the acquisition time of the high-quality moving image while suppressing the data capacity.

The high-quality moving image acquisition unit 219 performs predetermined image processing including a change in resolution on the acquired captured image data for a predetermined time, generates a high-quality moving image compressed by a predetermined moving image compression method, and acquires high-quality moving image data. The high-quality moving image data is image data having a high resolution, for example, 1980×1080 (full HD) or the like, equal to or higher than that of the still image data. The high-quality moving image acquisition unit 219 stores the acquired high-quality moving image data in the image DB 222 as a high-quality moving image file in a predetermined file format, for example, MP4, MXF, or the like. In this case, the high-quality moving image acquisition unit 219 stores the high-quality moving image data in association with the subject identification information in the storage unit 22.

In another embodiment, the high-quality moving image acquisition unit 219 may acquire captured image data output from the image processing unit 211 at predetermined intervals from the start to the end of the examination, and generate a high-quality moving image file limited to a predetermined time according to an instruction of the determination unit 215. The high-quality moving image acquisition unit 219 acquires high-quality moving image data based on captured image data for a predetermined time starting from a timing at which the instruction of the determination unit 215 is acquired, for example. Alternatively, the high-quality moving image acquisition unit 219 may acquire high-quality moving image data based on captured image data for a predetermined time acquired by going back a predetermined time length from the timing at which the instruction of the determination unit 215 is acquired.

Note that, in a case where each of the above-described image files is output and stored in an electronic medical record system or the like, it is desirable that each of the image files be stored in a format according to the electronic medical record system. Each of the image files may be stored according to, for example, the Digital Imaging and Communications in Medicine (DICOM) standard.

Figure 5:
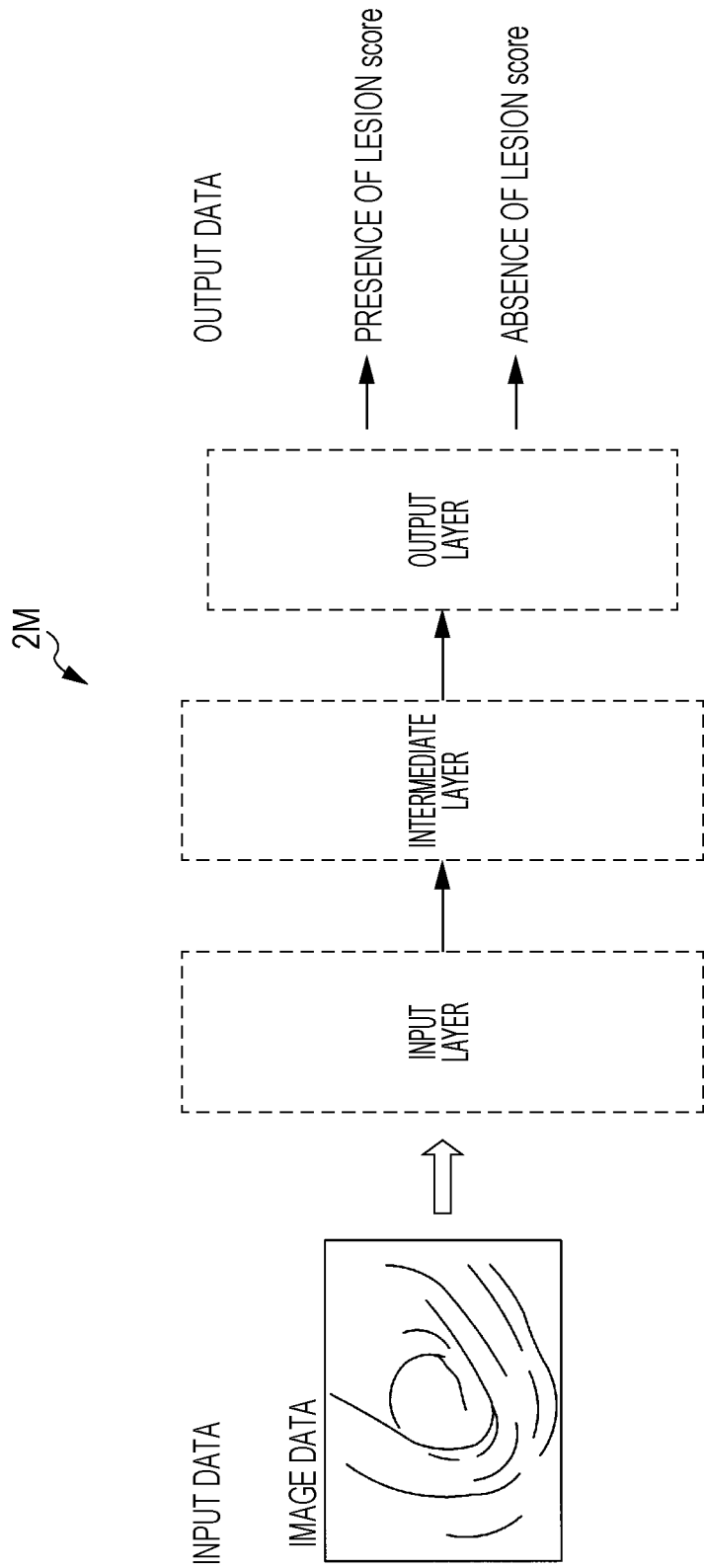
FIG. 5 is an explanatory diagram illustrating a configuration of a learning model.

Here, the learning model 2M will be described in detail. FIG. 5 is an explanatory diagram illustrating a configuration of the learning model 2M. The learning model 2M is generated and learned in advance by deep learning using a neural network in the processor 2 for an endoscope or an external device. The learning algorithm is, for example, a convolution neural network (CNN).

In the example illustrated in FIG. 5, the learning model 2M includes an input layer that receives an input of image data, an output layer that outputs an identification result of the presence or absence of a lesion, and an intermediate layer (hidden layer) that extracts a feature amount. The intermediate layer includes a plurality of nodes that extract feature amounts of input data, and passes the feature amounts extracted using various parameters to the output layer. When the image data is input to the input layer, calculation is performed in the intermediate layer using the learned parameters, and output information indicating the presence or absence of the lesion is output from the output layer.

The output information that is an identification result of the presence or absence of the lesion is output from the output layer of the learning model 2M. The output layer includes nodes respectively corresponding to the presence of the lesion and the absence of the lesion, which are set identification results, and outputs the accuracy for each of the presence of a lesion and the absence of a lesion as a score. The control unit 21 can set an identification result with a high score or an identification result with a score equal to or higher than a threshold as an output value of the output layer. Note that the output layer may have one output node that outputs an identification result with the highest accuracy instead of having the plurality of output nodes that output the accuracy of each identification result.

The control unit 21 performs learning using a large amount of image data and data obtained by collecting diagnosis results of endoscopic examinations performed in the past. The control unit 21 collects an information group in which information indicating the presence or absence of the lesion, which is a known diagnosis result, has been added to input information obtained from endoscopic examinations performed so far as training data in advance, and learns the learning model 2M. The control unit 21 learns the various parameters, weights, and the like constituting the learning model 2M using, for example, an error back propagation method so as to output the output information indicating the presence or absence of the lesion according to the endoscopic image data.

Although the example in which the learning model 2M is CNN has been described above, the learning model 2M is not limited to the CNN. In a case where time-series data is acquired, a neural network other than the CNN, for example, a recurrent neural network (RNN) or a long short term memory (LSTM) network may be used. The learning model 2M may be a segmentation network that extracts a region of a lesion portion. In addition, the learning model 2M may be a model trained by another algorithm, such as a support vector machine or a regression tree, which does not use a neural network.

Although the example in which the lesion detection unit 213 detects the presence or absence of the lesion in the endoscopic image using the learning model 2M has been described in the present embodiment, a method for detecting the lesion is not limited thereto. The lesion detection unit 213 may determine whether a lesion is included in an endoscopic image based on a feature amount of the endoscopic image and a feature amount of a lesion portion stored in advance, for example, using a method such as pattern matching or edge detection.

Figure 6:
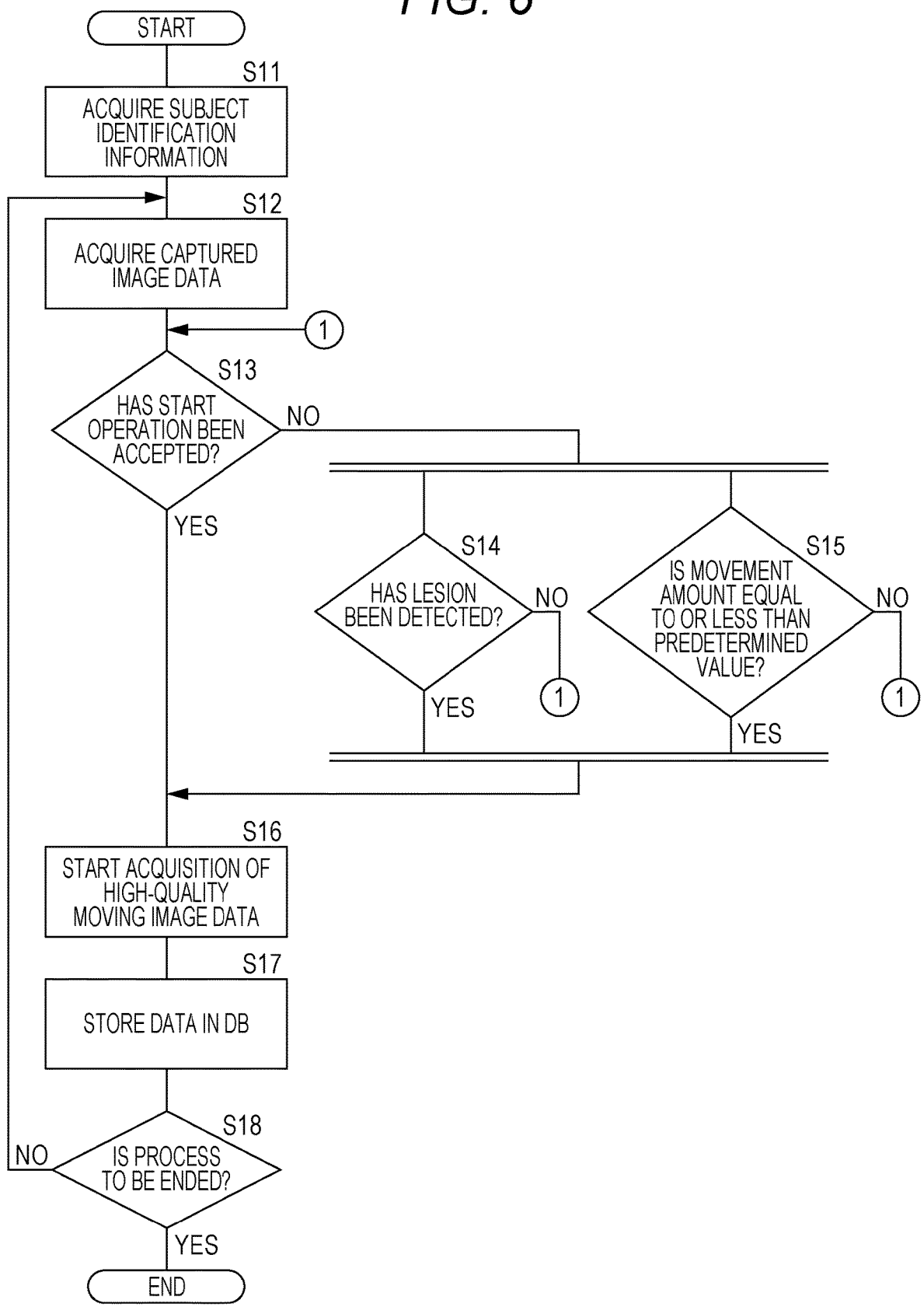
FIG. 6 is a flowchart illustrating an example of a processing procedure executed by the processor for an endoscope.

FIG. 6 is a flowchart illustrating an example of a processing procedure executed by the processor 2 for an endoscope. The control unit 21 of the processor 2 for an endoscope executes the processing illustrated in FIG. 6 in parallel with processing such as generation of an endoscopic image and generation of a low-quality moving image. For example, the control unit 21 executes the following processing based on an input content from the input unit 23 connected to the own device.

The control unit 21 acquires subject identification information through the input unit 23 by accepting an input operation of, for example, a keyboard, a touch panel, or the like (step S11).

The control unit 21 acquires captured image data from the endoscope 1 (step S12). Next, the control unit 21 determines whether a start condition is satisfied. The control unit 21 determines whether a start operation has been accepted as a first start condition (step S13). The control unit 21 executes a process of acquiring an operation signal according to a pressing operation of the control button 121 and outputting information indicating acceptance of the start operation using the acceptance unit 212. When the information indicating the acceptance of the start operation is acquired and it is determined that the start operation has been accepted (step S13: YES), the control unit 21 determines that the first start condition is satisfied and advances the processing to the start of acquisition of high-quality moving image data in step S16.

When the information indicating the acceptance of the start operation is not acquired and it is determined that the start operation has not been accepted (step S13: NO), the control unit 21 determines that the first start condition is not satisfied and advances the processing to determination of other start conditions in steps S14 and S15.

The control unit 21 determines whether a lesion has been detected from a captured image as a second start condition (step S14).

The control unit 21 executes processing of outputting information indicating a lesion detection result by the lesion detection unit 213. Specifically, the control unit 21 inputs the captured image data to the learning model 2M to specify a lesion detection result to be output. The image data input to the learning model 2M may be image data obtained by performing various types of processing on the captured image data, or may be endoscopic image data. When a lesion detection result indicating the presence of the lesion is acquired and it is determined that the lesion has been detected (step S14: YES), the control unit 21 determines that the second start condition is satisfied and advances the processing to the start of acquisition of high-quality moving image data in step S16.

On the other hand, when a lesion detection result indicating the absence of the lesion is acquired and it is determined that no lesion is detected (step S14: NO), the control unit 21 determines that the second start condition is not satisfied and returns the processing to step S13 to stand by until the start condition is satisfied.

The control unit 21 generates sub-processes and performs the process of step S15 in parallel with the process of step S14. The control unit 21 may perform inter-process communication in these two processes to achieve synchronization of processing. The control unit 21 determines whether a movement amount of the endoscope 1 is equal to or less than a predetermined value as a third start condition (step S15). The control unit 21 executes a process of outputting information indicating a movement amount detection result using the movement amount detection unit 214 based on the captured image data. The control unit 21 determines a magnitude relationship between the movement amount in the acquired movement amount detection result and the preset threshold. When it is determined that the movement amount is equal to or less than the predetermined value (step S15: YES), the control unit 21 determines that the third start condition is satisfied and advances the processing to the start of acquisition of high-quality moving image data in step S16.

On the other hand, when it is determined that the movement amount is not equal to or less than the predetermined value (step S15: NO), the control unit 21 determines that the third start condition is not satisfied, and returns the processing to step S13 to stand by until the start condition is satisfied.

When it is determined that any one of the first start condition to the third start condition is satisfied, the control unit 21 starts to acquire high-quality moving image data (step S16). The control unit 21 acquires captured image data for a predetermined time, set by accepting an input by the operator, from an acquisition start timing. An acquisition time of the high-quality moving image data is acquired. The control unit 21 performs predetermined image processing on the acquired captured image data and generates a high-quality moving image compressed by a predetermined moving image compression method to acquire the high-quality moving image data. The control unit 21 stores the high-quality moving image data in association with the subject identification information in the image DB (step S17).

The control unit 21 determines whether to end the process (step S18). For example, when the operator gives an instruction on the end of the endoscopic examination, or when the endoscope 1 is removed from the processor 2 for an endoscope, the control unit 21 determines to end the process. When it is determined not to end the processing (step S18: NO), the control unit 21 returns the processing to step S12 and continues to acquire captured image data. In this case, the control unit 21 may acquire the next captured image data at a timing when the acquisition of the high-quality moving image having a predetermined time length has ended. Alternatively, the control unit 21 may acquire the next captured image data before the acquisition of the high-quality moving image ends, and proceed with the process of determining the start condition. When it is determined to end the processing (step S18: YES), the control unit 21 ends the series of processes.

Note that each processing sequence described in the above embodiment is not limited, and the procedure can be changed as long as there is no contradiction in properties. Regarding the above processing sequences, for example, the order of execution of the respective processing steps may be changed, a plurality of the processing steps may be executed simultaneously, or the order of the respective processing steps may be different every time the series of processing sequences is executed. The control unit 21 may simultaneously determine the first to third start conditions described above. That is, the control unit 21 may perform the processes of step S14 and step S15 in parallel with the process of step S13.

In addition, an example in which the control unit 21 determines all the start conditions including the first start condition to the third start condition has been described in the above description, but the present embodiment is not limited thereto. For example, the control unit 21 may accept selection of any start condition among the first start condition to the third start condition for which a determination is performed, and perform a determination only for the selected start condition. The control unit 21 acquires necessity of the determination for each of the start conditions by, for example, accepting an input operation on a keyboard, a touch panel, or the like through the input unit 23. The control unit 21 executes the process of determining whether the start condition is satisfied only for the selected start condition, and acquires a high-quality moving image when the selected start condition is satisfied.

Furthermore, for example, the control unit 21 may be configured to accept selection of a threshold for the start condition per examination, and acquire a high-quality moving image according to the start condition including the selected threshold. For example, in the determination of the third start condition in step S15, the control unit 21 determines a magnitude relationship with a movement amount threshold selected and set in advance by the operator. Furthermore, the control unit 21 may perform a determination including a magnitude relationship with a threshold for the lesion detection accuracy even in the determination of the second start condition in step S14. In step S14, the control unit 21 acquires the presence or absence of a lesion and the detection accuracy as the lesion detection result. The detection accuracy is determined, for example, based on the score of the output information of the learning model 2M. When the lesion detection result indicates the presence of the lesion and the acquired detection accuracy is larger than a preset threshold, the control unit 21 determines that the second start condition is satisfied and acquires a high-quality moving image.

The operator can select the amount of information to be acquired according to a diagnosis content at the time of performing the examination or at a later date.

According to the present embodiment, the high-quality moving image is acquired in addition to the conventional still image and low-quality moving image in the processor 2 for an endoscope. Since the high-quality moving image is recorded with the resolution equal to or higher than that of the still image while being limited to the predetermined time length, it is possible to store the high-quality moving image with the limited data capacity for one examination. Even in a case where the doctor makes a diagnosis at a later date, the diagnosis can be made based on a still image recorded with a high image quality and a high-quality moving image limited only to a necessary time, and it is possible to efficiently make the diagnosis with high accuracy.

The high-quality moving image is not only acquired simultaneously with the still image in response to the instruction from the operator but also automatically acquired based on the predetermined start condition. Therefore, it is possible to prevent omission of an image, overlooking of a lesion, and the like, and to reduce the probability of occurrence of an erroneous diagnosis. Furthermore, it is possible to limitedly collect the high-quality moving image in which a target portion having a high possibility of the lesion is recorded with a high resolution, it is possible to efficiently collect information that can be used for, for example, training data of a machine learning model that outputs information regarding the lesion.

Second Embodiment

In a second embodiment, a configuration in which a plurality of high-quality moving images are provided as one connected moving image will be described. Hereinafter, a difference between the second embodiment and the first embodiment will be described. Since the other configurations except configurations to be described later are similar to the endoscope system of the first embodiment, the same reference signs are given to the common configurations, and the detailed description thereof will be omitted.

Figure 7:
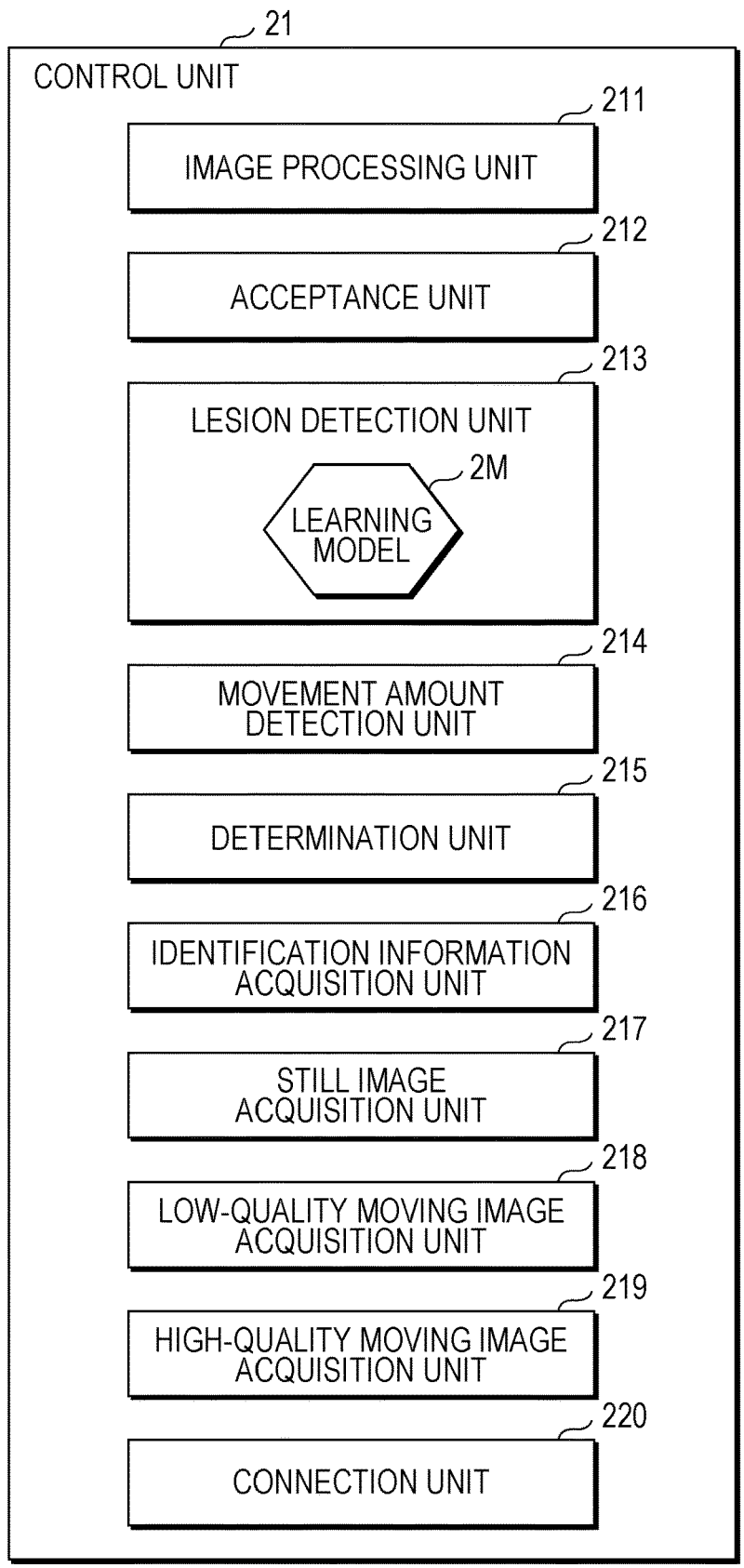
FIG. 7 is a functional block diagram of a processor for an endoscope according to a second embodiment.

FIG. 7 is a functional block diagram of the processor 2 for an endoscope according to the second embodiment. In the second embodiment, the control unit 21 of the processor 2 for an endoscope is configured to further function as a connection unit 220 by executing the program 2P stored in the storage unit 22.

In the second embodiment, the determination unit 215 instructs the image processing unit 211 to start outputting captured image data and issues a time stamp indicating a time point at which the captured image data has been output, at a timing when it is determined to acquire each piece of image data such as still image data, low-quality moving image data, and high-quality moving image data. The determination unit 215 outputs the issued time stamp to each of the still image acquisition unit 217, the low-quality moving image acquisition unit 218, and the high-quality moving image acquisition unit 219. Note that the determination unit 215 may output the time stamp to the image processing unit 211, and the image processing unit 211 may output the time stamp to each of the still image acquisition unit 217, the low-quality moving image acquisition unit 218, and the high-quality moving image acquisition unit 219. Each of the still image acquisition unit 217, the low-quality moving image acquisition unit 218, and the high-quality moving image acquisition unit 219 stores the acquired time stamp in the image DB 222 in association with each image file, thereby adding the time stamp to each image file. Alternatively, the still image acquisition unit 217, the low-quality moving image acquisition unit 218, and the high-quality moving image acquisition unit 219 may be configured to add a time stamp to each image file by embedding the time stamp in each image file to be generated. Note that time information is not limited to those included in each image file, and it is sufficient that the time information is stored in the image DB 222 in association with each image. For example, data of the time information may be stored in the image DB 222 in association with the image file.

Furthermore, the determination unit 215 outputs information indicating a start condition serving as a basis of the determination to the high-quality moving image acquisition unit 219 together with an instruction to start the output of high-quality moving image data. The high-quality moving image acquisition unit 219 stores the acquired information indicating the start condition in the storage unit 22 in association with the high-quality moving image data.

The connection unit 220 connects a plurality of pieces of the high-quality moving image data captured for the same subject to generate one piece of connected moving image data. The connection unit 220 refers to the image DB 222 and acquires the plurality of pieces of high-quality moving image data associated with the same subject identification information. The connection unit 220 arranges the plurality of pieces of high-quality moving image data in time series based on time information associated with each piece of the acquired high-quality moving image data. The connection unit 220 connects the last frame of high-quality moving image data at a previous time point and the first frame of high-quality moving image data at a subsequent time point between the high-quality moving image data adjacent in time series, thereby generating one piece of the connected moving image data.

In the above-described case of connecting the previous and subsequent frames, the connection unit 220 may perform interpolation between the previous and subsequent frames and connect the previous and subsequent frames. For example, in a case where a plurality of high-quality moving images obtained by capturing the same target location are acquired based on the same start condition, it is preferable to perform frame interpolation of the plurality of moving images to display smooth moving image data. The connection unit 220 further acquires high-quality moving image data associated with the same start condition from the plurality of pieces of high-quality moving image data acquired for the same subject. The connection unit 220 performs the interpolation of the previous and subsequent frames between pieces of the high-quality moving image data associated with the same start condition. In this case, the connection unit 220 may execute the frame interpolation when an acquisition time difference between the previous and subsequent frames is equal to or less than a predetermined value such as 0.1 seconds to 1 second. When an interval between the acquisition times of the previous and subsequent frames is more than the predetermined value, there is a high possibility that the both frames do not include the same capturing target, and thus, the connection unit 220 does not necessarily interpolate the frames.

The connection unit 220 performs interpolation for generating an intermediate frame based on, for example, previous and subsequent frames. Alternatively, the connection unit 220 may perform interpolation for generating an intermediate frame based on still image data or low-quality moving image data. In a case where still image data acquired at a time point between previous and subsequent frames is stored, the connection unit 220 may use the still image data as the intermediate frame. Alternatively, in a case where a frame of low-quality moving image data acquired at a time point between previous and subsequent frames is stored, the frame of the low-quality moving image data may be used as the intermediate frame. The connection unit 220 may specify the still image data or the low-quality moving image data to be used for the intermediate frame based on time information and subject identification information associated with the still image data or the low-quality moving image data.

Figure 8:
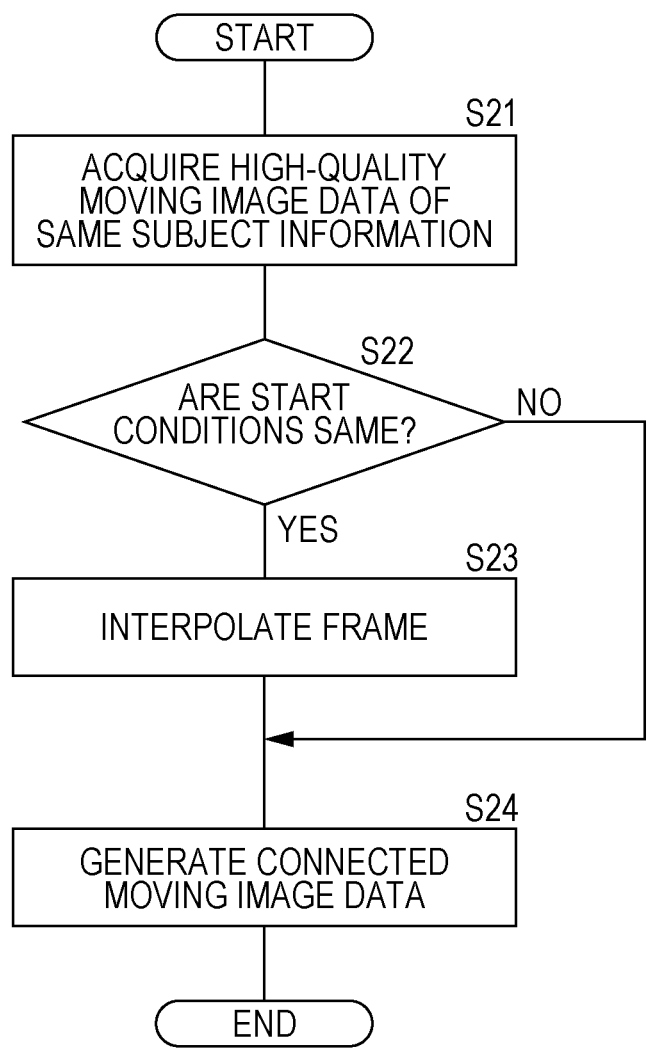
FIG. 8 is a flowchart illustrating an example of a connection processing procedure executed by the processor for an endoscope.

FIG. 8 is a flowchart illustrating an example of a connection processing procedure executed by the processor 2 for an endoscope. For example, the control unit 21 of the processor 2 for an endoscope executes the following processing based on an input content from the input unit 23 connected to the own device. The control unit 21 may execute the following processing at a timing when an examination is performed and new high-quality moving image data is stored.

The control unit 21 refers to the image DB 222 and acquires a plurality of pieces of high-quality moving image data associated with the same subject identification information (step S21). The control unit 21 arranges the plurality of pieces of high-quality moving image data in time series based on time information associated with each piece of the acquired high-quality moving image data.

The control unit 21 determines whether pieces of high-quality moving image data adjacent in time series have been acquired based on the same start condition (step S22). When start conditions of the consecutive pieces of high-quality moving image data do not match and it is determined that the start conditions are not the same (step S22: NO), the control unit 21 skips a frame interpolation process of step S23.

When the start conditions of the consecutive pieces of high-quality moving image data match and it is determined that the start conditions are the same (step S22: YES), the control unit 21 interpolates a frame (step S23). Specifically, the control unit 21 performs interpolation of the last frame of high-quality moving image data at a previous time point and the first frame of high-quality moving image data at a subsequent time point between the pieces of high-quality moving image data adjacent in time series. The control unit 21 executes the above process between a plurality of pieces of high-quality moving image data having the same start condition and consecutive in time series.

Among the plurality of pieces of high-quality moving image data associated with the same subject identification information, the control unit 21 connects the last frame of high-quality moving image data at a previous time point and the first frame of high-quality moving image data at a subsequent time point for each piece of the high-quality moving image data arranged in time series to generate one piece of connected moving image data (step S24). The control unit 21 displays the connected moving image data thus generated on the display device 3 through the output unit 24, and ends the series of processes. The control unit 21 may store the connected moving image data thus generated in the storage unit 22.

According to the present embodiment, the moving images acquired for the same subject are displayed as the series of connected moving images, and thus, a smoother diagnosis can be performed. In addition, the doctor can make a diagnosis without feeling missing of a frame by performing the frame interpolation in the moving images having the same start condition.

In each of the above embodiments, the endoscope 1 has been described as an example of a medical endoscope used for a subject who is a human, but the endoscope 1 may be an industrial endoscope used for an examination of a pipe or the like, for example.

Note that the embodiments disclosed as described above should be considered to be exemplary in all respects without being limited. The technical features described in the embodiments can be combined with each other, and the scope of the present invention is intended to include all modifications within the scope of the claims and the scope equivalent to the claims.

REFERENCE SIGNS LIST

1 Endoscope
2 Processor for endoscope
21 Control unit
22 Storage unit
2P Program
2A Recording medium
2M Learning model
222 Image DB
211 Image processing unit
212 Acceptance unit
213 Lesion detection unit
214 Movement amount detection unit
215 Determination unit
216 Identification information acquisition unit
217 Still image acquisition unit
218 Low-quality moving image acquisition unit
219 High-quality moving image acquisition unit
220 Connection unit

The invention claimed is:

1. A processor for an endoscope, comprising:
a determination processor that determines whether a start condition for starting acquisition of a moving image, which is limited to a predetermined time length and has a resolution equal to or higher than a resolution of a still image captured by an endoscope, is satisfied;
a moving image acquisition processor that starts the acquisition of the moving image when the determination processor determines that the start condition is satisfied; and
a movement amount detection processor that detects a movement amount of the endoscope based on the still image,
wherein the determination processor determines that the start condition is satisfied when the movement amount detected by the movement amount detection processor is equal to or less than a predetermined value.

2. The processor for an endoscope according to claim 1, further comprising
an acceptance processor that accepts a start operation of giving an instruction to start the acquisition of the moving image,
wherein the determination processor determines that the start condition is satisfied when the start operation has been accepted by the acceptance processor.

3. The processor for an endoscope according to claim 2, wherein
the start condition includes another start condition other than acceptance of the start operation by the acceptance processor, and
the determination processor determines whether the another start condition is satisfied when the start operation has not been accepted by the acceptance processor.

4. The processor for an endoscope according to claim 1, further comprising
a memory that stores the moving image in association with subject identification information of a subject captured by the endoscope.

5. The processor for an endoscope according to claim 4, wherein
the memory stores the start condition in association with the moving image.

6. The processor for an endoscope according to claim 4, further comprising
a connection processor that connects a plurality of the moving images, associated with identical subject identification information stored in the memory, in time series.

7. The processor for an endoscope according to claim 6, wherein
when a plurality of the moving images consecutively acquired based on an identical start condition are connected, the connection processor interpolates a frame between the plurality of moving images and connects the plurality of moving images.

8. The processor for an endoscope according to claim 1, further comprising
a second moving image acquisition processor that acquires a second moving image captured by the endoscope from a start to an end of an examination by the endoscope,
wherein the moving image has the resolution higher than a resolution of the second moving image.

9. The processor for an endoscope according to claim 1, wherein
the resolution of the moving image is equal to or higher than High-Vision.

10. A processor for an endoscope, comprising:
a determination processor that determines whether a start condition for starting acquisition of a moving image, which is limited to a predetermined time length and has a resolution equal to or higher than a resolution of a still image captured by an endoscope, is satisfied;
a moving image acquisition processor that starts the acquisition of the moving image when the determination processor determines that the start condition is satisfied; and
a lesion detection processor that detects a lesion in the still image,
wherein the determination processor determines that the start condition is satisfied when the lesion is detected by the lesion detection processor.

11. A processor for an endoscope comprising:
a still image acquisition processor that acquires a still image captured by an endoscope;
a moving image acquisition processor that acquires a moving image, which is limited to a predetermined time length and has a resolution equal to or higher than a resolution of the still image, based on a predetermined start condition;
a movement amount detection processor that detects a movement amount of the endoscope based on the still image; and
a determination processor that determines that the start condition is satisfied when the movement amount detected by the movement amount detection processor is equal to or less than a predetermined value.

12. The processor for an endoscope according to claim 11, further comprising
a memory that stores the still image acquired by the still image acquisition processor in association with the moving image acquired by the moving image acquisition processor.

13. An information processing method comprising:
determining whether a start condition for starting acquisition of a moving image, which is limited to a predetermined time length and has a resolution equal to or higher than a resolution of a still image captured by an endoscope, is satisfied;
starting the acquisition of the moving image when it is determined that the start condition is satisfied; and
detecting a movement amount of the endoscope based on the still image,
wherein the determining comprises determining that the start condition is satisfied when the detected movement amount is equal to or less than a predetermined value.

14. A non-transitory computer-readable storage medium that stores an executable computer program causing a computer to execute processing comprising:
determining whether a start condition for starting acquisition of a moving image, which is limited to a predetermined time length and has a resolution equal to or higher than a resolution of a still image captured by an endoscope, is satisfied;
starting the acquisition of the moving image when it is determined that the start condition is satisfied; and
detecting a movement amount of the endoscope based on the still image,
wherein the determining comprises determining that the start condition is satisfied when the detected movement amount is equal to or less than a predetermined value.

* * * * *